US005690604A

United States Patent [19]

Barnett

[11] Patent Number: 5,690,604

[45] Date of Patent: Nov. 25, 1997

[54] SEXUAL APPLIANCE HAVING A PHALLIC DEVICE AND A DEVICE FOR MOUNTING THE SAME ONTO A SUPPORT STRUCTURE

[75] Inventor: Doyle Barnett, Montecito, Calif.

[73] Assignee: Topco Sales, San Fernando, Calif.

[21] Appl. No.: 621,105

[22] Filed: Mar. 22, 1996

[51] Int. Cl.⁶ .......... A61F 5/00

[52] U.S. Cl. .......... 600/38; 248/229.15

[58] Field of Search .......... 600/38, 41, 35; 248/229.12, 229.15, 229.22, 229.25; 601/70, 78; D8/73

[56] References Cited

U.S. PATENT DOCUMENTS

| | | | |
|---|---|---|---|
| 1,232,690 | 6/1917 | Keenan | 248/229.15 |
| 4,722,327 | 2/1988 | Harvey | 600/41 |
| 4,903,929 | 2/1990 | Hoffman | 248/229.15 |
| 5,573,499 | 11/1996 | McAllister | 600/38 |

*Primary Examiner*—Jennifer Bahr

*Assistant Examiner*—Rosiland Kearney

*Attorney, Agent, or Firm*—Oppenheimer Poms Smith

[57] ABSTRACT

A sexual appliance that includes a phallic device and a support device having a first attachment member adapted to engage a support structure, such as a door, head board or bed post, and a second attachment member adapted to engage and support the phallic device.

24 Claims, 3 Drawing Sheets

SEXUAL APPLIANCE HAVING A PHALLIC DEVICE AND A DEVICE FOR MOUNTING THE SAME ONTO A SUPPORT STRUCTURE

BACKGROUND OF THE INVENTION

1. Field of Invention

The present invention is directed generally to the field of sexual appliances and, more particularly, to phallic devices such as dildos and vibrators.

2. Description of the Related Art

Phallic devices have been used as penis substitutes for many, many years. Such devices are primarily used for sexual pleasure, both by couples and by people who do not have a sex partner. Recently, the increase in serious sexually transmitted diseases such as AIDS has made the use of phallic devices even more common because they may be used as a penis substitute in safe sex practices. In addition, the development of modern plastics and other moldable materials has enabled the mass production of phallic devices in essentially any shape, texture or size. As a result, a wide variety of phallic devices are available. The shape is typically that of a smooth-edged contoured cylinder or a close replica of a human penis which is either flaccid or erect.

Phallic devices are used by couples when the male partner is impotent or simply as a sexual aid to enhance erotic experiences. When used by a person who does not have a sex partner, such devices are held with one or both hands. Unfortunately, the number of sexual activities that may be simulated by a user who does not have a partner is limited by that person's reach and the manner in which the shoulder and elbow joints are configured.

SUMMARY OF THE INVENTION

The general object of the present invention is to provide a sexual appliance that is superior than those previously known in the art. In particular, one object of the present invention is to provide a sexual appliance that may be used to simulate a wider variety of sexual activities and positions than sexual appliances previously known in the art. Another object of the present invention is to provide a sexual appliance which may be used in a hands-free manner.

In accordance with one aspect of the present invention, these and other objectives are accomplished by providing a sexual appliance which includes a phallic device (or penis substitute device), such as a dildo or vibrator, and a support device which secures the phallic device to a support structure. Such support structures include, but are not limited to, doors, head boards and bed posts. So secured, the phallic device may be used to simulate sexual activities which would be difficult, or even impossible to simulate if it the phallic device was held in one or both of the user's hands.

Many other features and attendant advantages of the present invention will become apparent as the invention becomes better understood by reference to the following detailed description considered in conjunction with the accompanying drawings.

BRIEF DESCRIPTION OF THE DRAWINGS

Detailed description of the preferred embodiments of the invention will be made with reference to the accompanying drawings.

DETAILED DESCRIPTION OF THE PREFERRED EMBODIMENT

The following is a detailed description of the best presently known mode of carrying out the invention. This description is not to be taken in a limiting sense, but is made merely for the purpose of illustrating the general principles of the invention. The scope of the invention is defined solely by the appended claims.

Figure 1:
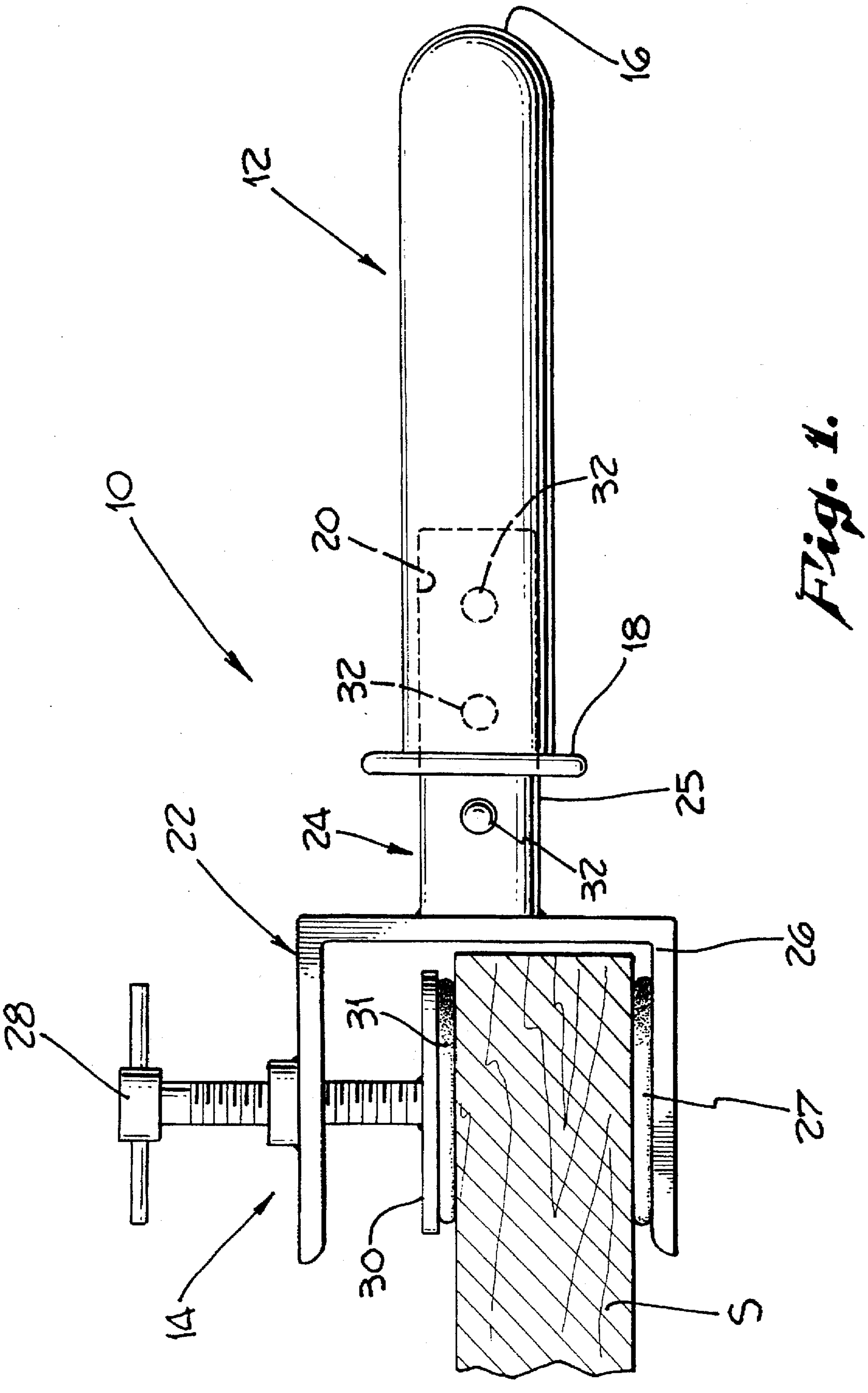
FIG. 1 is a top view of a sexual appliance in accordance with a preferred embodiment of the present invention.

As illustrated in FIG. 1, a sexual appliance 10 in accordance with a preferred embodiment of the present invention includes phallic device 12 and a support device 14 which mounts the phallic device on a support structure S. Examples of support structures which may be used in conjunction with the present invention include doors, head boards and bed posts. In the embodiment shown in FIG. 1, the phallic device 12 is in the form of a dildo having a forward end 16 and a rearward end 18. The rearward end includes a longitudinally extending aperture 20. Phallic device 12 may be formed from any suitable substantially resilient material, but is preferably composed of a resilient rubber-like material, such as polyvinyl chloride. Such materials may be molded to the desired size, shape and texture. The material should also be washable. If so desired, forward end 16 can be manufactured such that it is more flexible than rearward end 18 in order to reduce the likelihood of injury to the user. Support device 14 is preferably formed from a rigid plastic material, but may also be formed from metal or from a combination of the two.

The exemplary support device 14 shown in FIG. 1 includes a first attachment member 22 and a second attachment member 24. The first attachment member 22 is, in the illustrated example, a clamp that includes a C-shaped member 26, a resilient cushion 27 to protect the support structure, a threaded tightening bolt 28 and a head 30. The head is preferably a swivel-type head that includes a resilient covering 31, also to prevent damage to the support structure. Turning to the exemplary second attachment member 24, it includes a longitudinally extending arm 25 having a series of detents 32. The length of the arm may vary depending on the type and size of the phallic device used therewith and the desired distance of the phallic device from the support structure. The detents engage the inner surface of the elongate aperture 20 formed in phallic device 12. Although the detents may be any suitable shape and can be either round or have sharp corners, the detents must be configured such that they will engage the inner surface of the aperture to such an extent that the phallic device will not be pulled from arm 25 during use. However, they should not engage the inner surface to such an extent that the phallic device cannot be removed from support device 14 for cleaning or replacement. In addition, a single support device to may be used to support a variety of phallic devices having different sizes, shapes and textures, thereby increasing the flexibility of the appliance.

Figure 2:
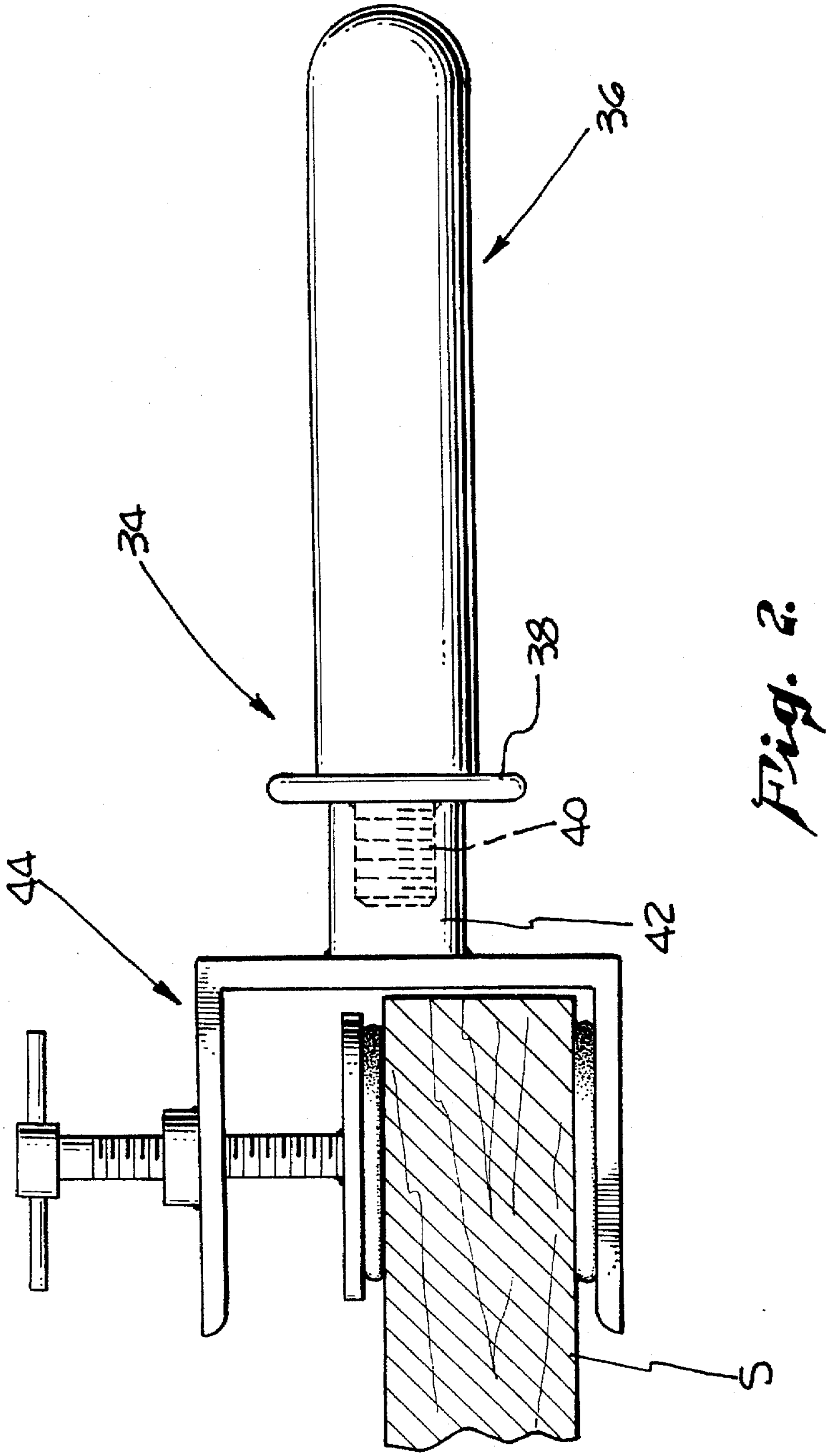
FIG. 2 is top view of a sexual appliance in accordance with another preferred embodiment of the present invention.

The preferred embodiment shown in FIG. 1 is susceptible to numerous modifications without departing from the spirit and scope of the present invention. In the exemplary sexual appliance 34 shown in FIG. 2, a phallic device 36 is configured such that its rearward end 38 includes an attachment member 40 which mates with a corresponding attachment member 42 on support device 44. Although the illustrated attachment members are threaded, they may also be configured for a snap-fit connection or any other suitable mechanical connection. Other modifications within the scope of the present invention concern first attachment member 22. For example, resilient cushion 27, the portion of C-shaped member 26 supporting the resilient cushion and/or head 30 may be reconfigured so that they have a curved surface. The support device will then be better suited for curved support structures, such as bed posts. Additionally, the exemplary C-clamp and threaded bolt arrangement shown in FIG. 1 may be entirely eliminated and replaced by a spring biased clamp or any other suitable clamping device.

Figure 3:
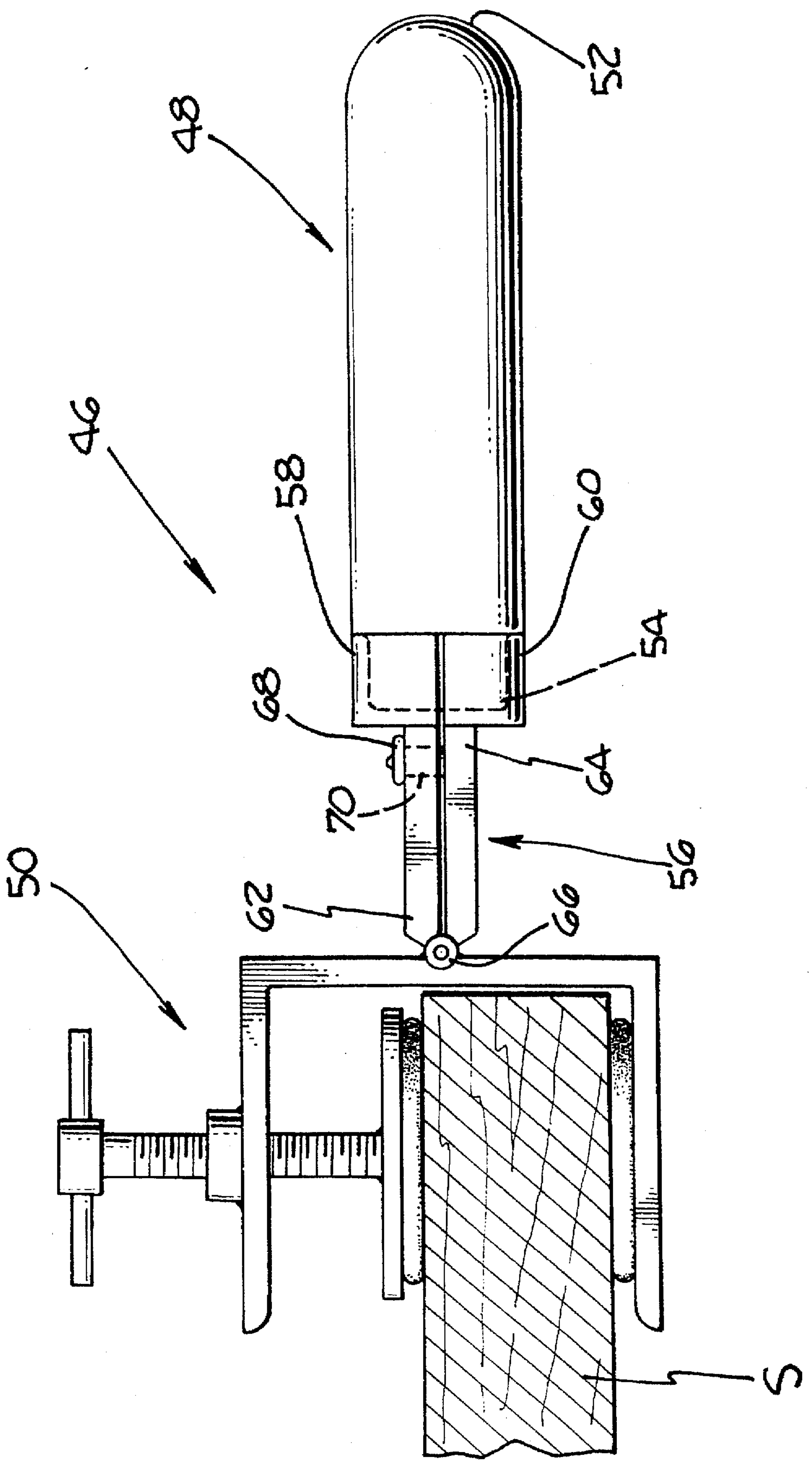
FIG. 3 is a top view of a sexual appliance in accordance with still another preferred embodiment of the present invention.

Another exemplary embodiment of the present invention is shown in FIG. 3. Referring to the numbered elements in FIG. 3, a sexual appliance 46 includes a phallic device 48 and a support device 50 which secures the phallic device to support structure S. The phallic device shown in FIG. 3, which may be either an electric vibrator or a dildo, has a forward end 52 and a rearward end 54. The rearward end of the phallic device is secured to the support device by a clamp 56. The clamp includes a pair of curved holding members 58 and 60, which completely enclose, and frictionally engage, the rearward end of the phallic device. If so desired, the diameter of the rearward end of the phallic device may be slightly smaller than the remaining portion (as shown) so that there is a smooth transition between the curved holding members and the remaining portion of the phallic device. Also, the inner surface of the holding members may include a sheet of rubber or rubber-like material to increase friction and protect the rearward end of the phallic device.

The curved holding members are respectively mounted on arms 62 and 64. The arms are pivotally connected to one another by a hinge 66 which is secured to the portion of support device 50 which secures the support device to the support structure. This aspect of support device 50 is essentially the same as the exemplary devices described above with reference to FIGS. 1 and 2. Arm 62 includes a rotatable locking tab 68 that is mounted on a stem 70. The locking tab is configured such that its length is greater than its width. Arm 64 includes a corresponding aperture (not shown) which allows the locking tab 68 to pass when the clamp is moved from an open position to the closed position shown in FIG. 3. The aperture is also longer than it is wide and its width is less than the length of the locking tab.

To lock phallic device 48 into place, its rearward end 54 is placed between holding members 58 and 60. When the holding members are moved to the position shown in FIG. 3, locking tab 68 will extend completely through arm 62. A one-quarter turn rotation of the locking tab will cause the longitudinal ends of the tab to extend beyond the sides of the aperture. This will prevent arms 62 and 64 from spreading apart and lock phallic device 48 into place.

The illustrated locking tab arrangement is only one example of a mechanism that may be used to maintain holding members 58 and 60 in the closed position shown in FIG. 3. Other locking mechanisms, such as a separate clamp or a spring biased locking device, may also be used.

Although the present invention has been described in terms of the preferred embodiments above, numerous modifications and/or additions to the above-described preferred embodiments would be readily apparent to one skilled in the art. It is intended that the scope of the present invention extends to all such modifications and/or additions and that the scope of the present invention is limited solely by the claims set forth below.

What is claimed is:

1. A sexual appliance, comprising:

a resilient phallic device defining a forward end, a rearward end and a longitudinally extending aperture extending from the rearward end to a point between the rearward end and the forward end; and a support device including a clamp having a substantially C-shaped member and a threaded tightening bolt, an arm operably connected to the C-shaped member and extending longitudinally therefrom, and a plurality of detents associated with the arm and adapted to engage a surface of the longitudinally extending aperture of the resilient phallic device;

wherein the resilient phallic device is positioned over at least a portion of the longitudinally extending arm and at least one of the detents when the appliance is in an assembled state.

2. A sexual appliance, comprising:

a penis substitute device defining a longitudinal axis extending from a forward end and a rearward end thereof; and a support device including a first attachment member including a rotatable tightening element and at least two contact surfaces adapted to engage respective surfaces of a support structure defining a longitudinal axis, and a second attachment member adapted to engage and support the penis substitute device, the support device supporting the penis substitute device such that the longitudinal axis of the penis substitute device intersects and is substantially perpendicular to the longitudinal axis of the support structure, the tightening element and contact surfaces being arranged such that rotation of the tightening element will move the contact surfaces relative to one another.

3. A sexual appliance, comprising:

a penis substitute device defining a forward end, a rearward end and a longitudinally extending aperture extending from the rearward end to a point between the rearward end and the forward end; and a support device including a first attachment member adapted to engage a support structure and a second attachment member adapted to engage and support the penis substitute device, the second attachment member including a longitudinally extending arm, wherein at least a portion of the longitudinally extending aperture is positioned over the arm when the appliance is in an assembled state.

4. A sexual appliance as claimed in claim 3, wherein the longitudinally extending arm includes at least one detent.

5. A sexual appliance, comprising:

a penis substitute device defining a forward end and a rearward end; and a support device including a clamp adapted to engage a support structure and a support device attachment member adapted to engage and support the penis substitute device.

6. A sexual appliance as claimed in claim 5, wherein the clamp includes a C-shaped member and a threaded tightening bolt.

7. A sexual appliance as claimed in claim 6, wherein the threaded tightening bolt includes a head for contacting the support structure.

8. A sexual appliance as claimed in claim 2, wherein the penis substitute device includes a penis substitute device attachment member operably connected to the rearward end of the penis substitute device, the penis substitute device attachment member being adapted to mechanically engage the second attachment member of the support device.

9. A sexual appliance as claimed in claim 8, wherein the penis substitute device attachment member and the second attachment member of the support device each include threads.

10. A sexual appliance as claimed in claim 2, wherein the penis substitute device comprises a prosthetic penis appliance formed from a resilient material.

11. A sexual appliance as claimed in claim 2, wherein the penis substitute device comprises an electric vibrator.

12. A sexual appliance, comprising:

a penis substitute device defining a forward end and a rearward end; and a support device including a first attachment member adapted to engage a support structure and a clamp adapted to engage and support the penis substitute device, the clamp including first and second pivotable arms which define separate structural members, said arm pivot about a hinge and define longitudinal ends, and first and second curved holding members respectively operably connected to the longitudinal ends of the first and second arms.

13. A sexual appliance as claimed in claim 12, wherein the clamp further includes a locking device.

14. A sexual appliance, comprising:

a penis substitute device defining a forward end and a rearward end; and a clamp operably connected to at least the rearward end of the penis substitute device and adapted to engage a support structure and secure the penis substitute device thereto.

15. A sexual appliance as claimed in claim 14, wherein the clamp comprises a rotatable tightening element.

16. A sexual appliance as claimed in claim 15, wherein the rotatable tightening element comprises a threaded bolt.

17. A sexual appliance as claimed in claim 15, wherein the clamp includes at least two clamping surfaces and the clamping surfaces move relative to one another in response to rotation of the tightening element.

18. A sexual appliance as claimed in claim 14, further comprising:

a clamp attachment member operably connected to the clamp and adapted to engage the penis substitute device.

19. A sexual appliance as claimed in claim 18, wherein the penis substitute device includes a penis substitute device attachment member operably connected to the clamp attachment member.

20. A sexual appliance as claimed in claim 19, wherein the penis substitute device attachment member and the clamp attachment member each include threads.

21. A sexual appliance as claimed in claim 14, wherein the penis substitute device comprises a prosthetic penis appliance formed from a resilient material.

22. A sexual appliance as claimed in claim 14, wherein the penis substitute device comprises an electric vibrator.

23. A sexual appliance as claimed in claim 14, wherein the penis substitute device defines a longitudinal axis and the clamp engages a portion of the support structure such that the longitudinal axis of the penis substitute device is substantially perpendicular to the portion of the support structure.

24. A sexual appliance for use with a support structure, comprising:

a penis substitute device defining a forward end, a rearward end and a longitudinal axis extending outwardly from the forward end and the rearward end; and a clamp operably connected to the rearward end of the penis substitute device and adapted to engage the support structure and secure the penis substitute device thereto such that the longitudinal axis of the penis substitute device passes through the support structure.

* * * * *